(12) United States Patent
Fikes (10) Patent No.: US 9,155,636 B1
(45) Date of Patent: Oct. 13, 2015

(54) PROSTHETIC SOCKET LINER

(76) Inventor: Ray Fikes, Mesa, AZ (US)

( * ) Notice: Subject to any disclaimer, the term of this patent is extended or adjusted under 35 U.S.C. 154(b) by 155 days.

(21) Appl. No.: 13/486,863

(22) Filed: Jun. 1, 2012

Related U.S. Application Data (60) Provisional application No. 61/492,320, filed on Jun. 1, 2011.

(51) Int. Cl.
*A61F 2/80* (2006.01)

(52) U.S. Cl.
CPC ............. *A61F 2/80* (2013.01); *A61F 2002/802* (2013.01)

(58) Field of Classification Search
CPC A61F 2/80; A61F 2002/802; A61F 2002/805
USPC ..................................................... 623/32–37
See application file for complete search history.

(56) References Cited

U.S. PATENT DOCUMENTS

| | | |
|---|---|---|
| 2,530,285 A | 11/1950 | Catranis |
| 2,533,404 A | 12/1950 | Sharp |
| 2,790,180 A | 4/1957 | Hauser |
| 4,911,724 A | 3/1990 | Fikes |
| 5,007,937 A | 4/1991 | Fishman et al. |
| 5,163,965 A | 11/1992 | Rasmusson et al. |
| 5,258,037 A | 11/1993 | Caspers |
| 5,314,497 A | 5/1994 | Fay et al. |
| 5,376,132 A | 12/1994 | Caspers |
| 5,387,245 A | 2/1995 | Fay |
| 5,480,455 A | 1/1996 | Norvell |
| 5,534,034 A | 7/1996 | Caspers |
| 5,549,709 A | 8/1996 | Caspers |
| 5,571,208 A | 11/1996 | Caspers |
| 5,658,353 A | 8/1997 | Layton |
| 5,658,354 A | 8/1997 | Norvell |
| 5,724,714 A | 3/1998 | Love |
| 5,728,169 A | 3/1998 | Norvell |
| 5,728,170 A | 3/1998 | Becker et al. |
| 5,735,906 A | 4/1998 | Caspers |
| 5,888,216 A | 3/1999 | Haberman |
| 5,888,230 A | 3/1999 | Helmy |
| 5,904,722 A | 5/1999 | Caspers |
| 5,931,872 A | 8/1999 | Lohmann |
| 5,980,576 A | 11/1999 | Graf et al. |
| 5,980,577 A | 11/1999 | Radis et al. |
| 6,063,125 A | 5/2000 | Arbogast et al. |

(Continued)

FOREIGN PATENT DOCUMENTS

| | | |
|---|---|---|
| AU | 2002358395 | 6/2003 |
| DE | 2540138 | 3/1977 |

(Continued)

*Primary Examiner* — Bruce E Snow
(74) *Attorney, Agent, or Firm* — Adam R. Stephenson, Ltd.

(57) ABSTRACT

A prosthetic socket liner. A liner of the prosthetic socket liner has an inner and outer surface, the inner surface configured to engage skin of a user's residual limb and the outer surface configured to engage a surface of a socket of a prosthesis. An air channel coupled to the liner and to a valve extends downwardly towards a closed end of the liner and is configured to transfer air between an outer surface of the liner and ambient air through the valve. In implementations the air channel is configured to channel air between an inside of a cavity and a location outside the cavity. A method of donning a socket of a prosthesis includes donning a liner of a prosthetic socket liner over a residual limb, opening a valve on the liner, inserting the liner into a socket of a prosthesis with the valve open, and closing the valve.

15 Claims, 9 Drawing Sheets

(56) References Cited

U.S. PATENT DOCUMENTS

| | | | |
|---|---|---|---|
| D429,335 S | 8/2000 | Caspers et al. | |
| 6,149,691 A | 11/2000 | Fay et al. | |
| 6,231,616 B1 | 5/2001 | Helmy | |
| 6,231,617 B1 | 5/2001 | Fay | |
| 6,361,568 B1 | 3/2002 | Hoemer | |
| 6,454,812 B1 | 9/2002 | Laghi | |
| 6,508,842 B1 | 1/2003 | Caspers | |
| 6,544,292 B1 | 4/2003 | Laghi | |
| 6,554,868 B1 | 4/2003 | Caspers | |
| 6,626,952 B2 | 9/2003 | Janusson et al. | |
| 6,702,858 B2 | 3/2004 | Christensen | |
| 6,706,364 B2 | 3/2004 | Janusson | |
| 6,726,726 B2 | 4/2004 | Caspers | |
| 6,761,742 B2 | 7/2004 | Caspers | |
| 6,764,631 B1 | 7/2004 | Laghi | |
| 6,852,269 B2 | 2/2005 | Eberle et al. | |
| 6,918,936 B2 | 7/2005 | Hellberg | |
| 6,926,742 B2 | 8/2005 | Caspers | |
| 6,936,073 B2 * | 8/2005 | Karason | 623/37 |
| 6,942,703 B2 | 9/2005 | Carstens | |
| 6,964,688 B1 | 11/2005 | Kania | |
| 6,974,484 B2 | 12/2005 | Caspers | |
| 7,118,602 B2 | 10/2006 | Bjarnason | |
| 7,150,762 B2 | 12/2006 | Caspers | |
| 7,162,322 B2 | 1/2007 | Arbogast et al. | |
| 7,169,189 B2 | 1/2007 | Bjarnason et al. | |
| 7,235,108 B2 * | 6/2007 | Carstens | 623/36 |
| 7,344,568 B2 | 3/2008 | Chen | |
| 7,351,264 B2 | 4/2008 | Wilson | |
| 7,377,944 B2 | 5/2008 | Janusson et al. | |
| 7,427,297 B2 | 9/2008 | Patterson et al. | |
| 7,427,298 B1 | 9/2008 | Swanson, Sr. | |
| 7,431,738 B2 | 10/2008 | Perkins et al. | |
| 7,438,843 B2 | 10/2008 | Asgeirsson | |
| 7,479,162 B2 | 1/2009 | Kurth | |
| 7,575,561 B2 | 8/2009 | Smith et al. | |
| 7,632,315 B2 | 12/2009 | Egilsson | |
| 7,655,049 B2 | 2/2010 | Phillips | |
| 7,661,164 B2 | 2/2010 | Chen | |
| 7,662,191 B2 | 2/2010 | Asgeirsson | |
| 7,749,281 B2 | 7/2010 | Egilsson | |
| 7,771,487 B2 | 8/2010 | Mantelmacher | |
| 7,780,741 B2 | 8/2010 | Janusson et al. | |
| 7,842,099 B2 | 11/2010 | Mantelmacher | |
| 7,850,739 B2 | 12/2010 | Perkins et al. | |
| 7,883,547 B2 | 2/2011 | Mantelmacher | |
| 7,909,884 B2 | 3/2011 | Egilsson et al. | |
| 7,922,775 B2 | 4/2011 | Caspers | |
| 7,927,377 B2 | 4/2011 | Slemker et al. | |
| 7,927,378 B2 | 4/2011 | Scussel | |
| 2002/0002405 A1 | 1/2002 | Janusson et al. | |
| 2002/0165619 A1 | 11/2002 | Hellberg | |
| 2003/0113494 A1 | 6/2003 | Janusson et al. | |
| 2003/0178746 A1 | 9/2003 | Eberle et al. | |
| 2003/0181989 A1 | 9/2003 | Eberle et al. | |
| 2003/0216815 A1 | 11/2003 | Christensen | |
| 2004/0137178 A1 | 7/2004 | Janussen et al. | |
| 2004/0181290 A1 | 9/2004 | Caspers | |
| 2004/0260403 A1 | 12/2004 | Patterson et al. | |
| 2005/0119777 A1 | 6/2005 | Arbogast et al. | |
| 2005/0131549 A1 | 6/2005 | Caspers | |
| 2005/0149202 A1 | 7/2005 | Schaffer et al. | |
| 2005/0184619 A1 | 8/2005 | Chen | |
| 2005/0267598 A1 | 12/2005 | Bjarnason et al. | |
| 2007/0005149 A1 | 1/2007 | Egilsson et al. | |
| 2007/0055383 A1 * | 3/2007 | King | 623/34 |
| 2007/0061017 A1 | 3/2007 | Wilson | |
| 2007/0080479 A1 | 4/2007 | Arbogast et al. | |
| 2007/0112439 A1 | 5/2007 | Panucialman | |
| 2007/0112440 A1 | 5/2007 | Perkins et al. | |
| 2007/0255325 A1 | 11/2007 | de Vries | |
| 2008/0086218 A1 | 4/2008 | Egilsson | |
| 2008/0188948 A1 | 8/2008 | Flatt | |
| 2008/0188949 A1 | 8/2008 | MacKenzie | |
| 2009/0036999 A1 | 2/2009 | Egilsson et al. | |
| 2009/0182435 A1 * | 7/2009 | Haberman | 623/36 |
| 2009/0198346 A1 | 8/2009 | Perkins et al. | |
| 2009/0240344 A1 | 9/2009 | Colvin | |
| 2010/0016993 A1 | 1/2010 | MacKenzie | |
| 2010/0023134 A1 | 1/2010 | Laghi | |
| 2010/0076357 A1 | 3/2010 | Schneider | |
| 2010/0114238 A1 | 5/2010 | Muccio | |
| 2010/0125342 A1 | 5/2010 | King | |
| 2010/0185300 A1 | 7/2010 | Mackenzie | |
| 2010/0249949 A1 | 9/2010 | Bjarnason et al. | |
| 2010/0249950 A1 | 9/2010 | Bielefeld | |
| 2010/0274363 A1 | 10/2010 | Laghi et al. | |
| 2010/0318196 A1 | 12/2010 | Egilsson | |
| 2011/0022182 A1 | 1/2011 | Perkins et al. | |
| 2011/0022184 A1 | 1/2011 | Slemker et al. | |
| 2011/0029096 A1 | 2/2011 | Laghi | |
| 2011/0035027 A1 | 2/2011 | McCarthy | |
| 2011/0071648 A1 | 3/2011 | McKinney | |
| 2011/0071649 A1 | 3/2011 | McKinney | |
| 2011/0077748 A1 | 3/2011 | Egilsson et al. | |
| 2011/0092935 A1 | 4/2011 | Hann et al. | |
| 2011/0098827 A1 | 4/2011 | Laghi et al. | |
| 2011/0125291 A1 | 5/2011 | Tompkins et al. | |
| 2011/0144769 A1 | 6/2011 | Nakamura | |
| 2011/0196511 A1 * | 8/2011 | Slemker et al. | 623/34 |

FOREIGN PATENT DOCUMENTS

| | | |
|---|---|---|
| DE | 3508919 | 9/1986 |
| DE | 102006045517 | 4/2008 |
| EP | 1588244 | 9/2005 |
| EP | 1263358 | 6/2009 |
| EP | 1814480 | 9/2009 |
| EP | 1263356 | 1/2010 |
| IT | 1334240 | 5/2006 |
| KR | 2003011075 | 2/2003 |
| WO | WO0167842 | 9/2001 |
| WO | WO0170147 | 9/2001 |
| WO | WO0121113 | 11/2001 |
| WO | WO2010085336 | 7/2010 |

* cited by examiner

PROSTHETIC SOCKET LINER

CROSS REFERENCE TO RELATED APPLICATIONS

This document claims the benefit of the filing date of U.S. Provisional Patent Application 61/492,320, entitled "Air Channeling Liner" to Raymond Fikes which was filed on Jun. 1, 2011, the disclosure of which is hereby incorporated entirely herein by reference.

BACKGROUND

1. Technical Field

Aspects of this document relate generally to liners used in relation to prosthetic limbs.

2. Background Art

Liners are used in the field of prosthetic limbs. In instances a liner is placed over a residual limb prior to donning a socket of a prosthetic limb, and the liner forms a layer at least partially between the residual limb and the socket of the prosthetic limb. An example of a conventional liner may be found in U.S. Pat. No. 6,544,292 to Aldo A. Laghi entitled "Prosthetic liner with integral air expulsion valve," issued Apr. 8, 2003, the disclosure of which is incorporated entirely herein by reference.

SUMMARY

Implementations of prosthetic socket liners may include: a liner having an inner surface and an outer surface, the inner surface configured to engage with skin of a residual limb of a user and the outer surface configured to engage a surface of a socket of a prosthesis; and one or more air channels coupled to the liner and coupled to one or more valves, the one or more air channels extending downwardly towards a closed end of the liner, the one or more air channels configured to transfer air between the outer surface of the liner and ambient air through the one or more valves.

Implementations of prosthetic socket liners may include one, all, or any of the following:

The one or more air channels may be one of: coupled to the outer surface of the liner; coupled to the inner surface of the liner, and; within a sidewall located between the inner surface and outer surface of the liner.

The one or more air channels may be configured to transfer air between the inner surface of the liner and ambient air through the one or more valves.

A first socket engager may be coupled to the liner and configured to engage the surface of the socket.

The one or more valves may comprise a selective two-way valve.

The one or more air channels may transfer air from the closed end of the liner to proximate an open end of the liner.

A suspension member may be coupled to the liner between a first socket engager and the liner and may include one of an air bladder and a compressible foam.

A retainer may be coupled to the closed end of the liner and may be configured to bias the closed end of the liner towards the surface of the socket.

The liner may be formed of a substantially non-air-permeable material.

Implementations of prosthetic socket liners may include: a liner configured to engage a residual limb of a user, a first socket engager coupled to the liner and configured to engage a socket of a prosthesis; an air channel coupled to the liner and configured to channel air between an inside of a cavity and a location outside the cavity, the cavity located between the liner and the socket; and a valve coupled to the air channel and configured to selectively allow and disallow air to be channeled between inside the cavity and outside the cavity.

Implementations of prosthetic socket liners may include one, all, or any of the following:

A second socket engager may be coupled to the liner and configured to engage the socket.

The first socket engager may include a flexible, circular fin extending outwardly from the liner at an about 90 degree angle.

The valve may be a selective two-way valve.

The valve may be one of: a flap held closed by low pressure formed within the cavity; and a removable plug.

The air channel may channel air from a closed end of the liner to proximate an open end of the liner.

A suspension member may be coupled to the liner between the first socket engager and the liner.

The air channel may be one of: coupled to an outer surface of the liner; coupled to an inner surface of the liner, and; within a sidewall located between the inner surface and outer surface of the liner.

The liner may be formed of a substantially non-air-permeable material.

Implementations of a method of donning a socket of a prosthesis may include: donning a liner of a prosthetic socket liner over a portion of a residual limb of a user; opening a valve on the liner, inserting the liner into a socket of a prosthesis with the valve open: and closing the valve.

Implementations of a method of donning a socket of a prosthesis may include one, all, or any of the following:

Forming one of a lubricated surface and an air-tight seal between an outer surface of the liner and a surface of the socket.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components or assembly procedures disclosed herein. Many additional components and assembly procedures known in the art consistent with the intended prosthetic socket liners and/or assembly procedures for prosthetic socket liners will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such prosthetic socket liners and implementing components, consistent with the intended operation.

Figure 1:
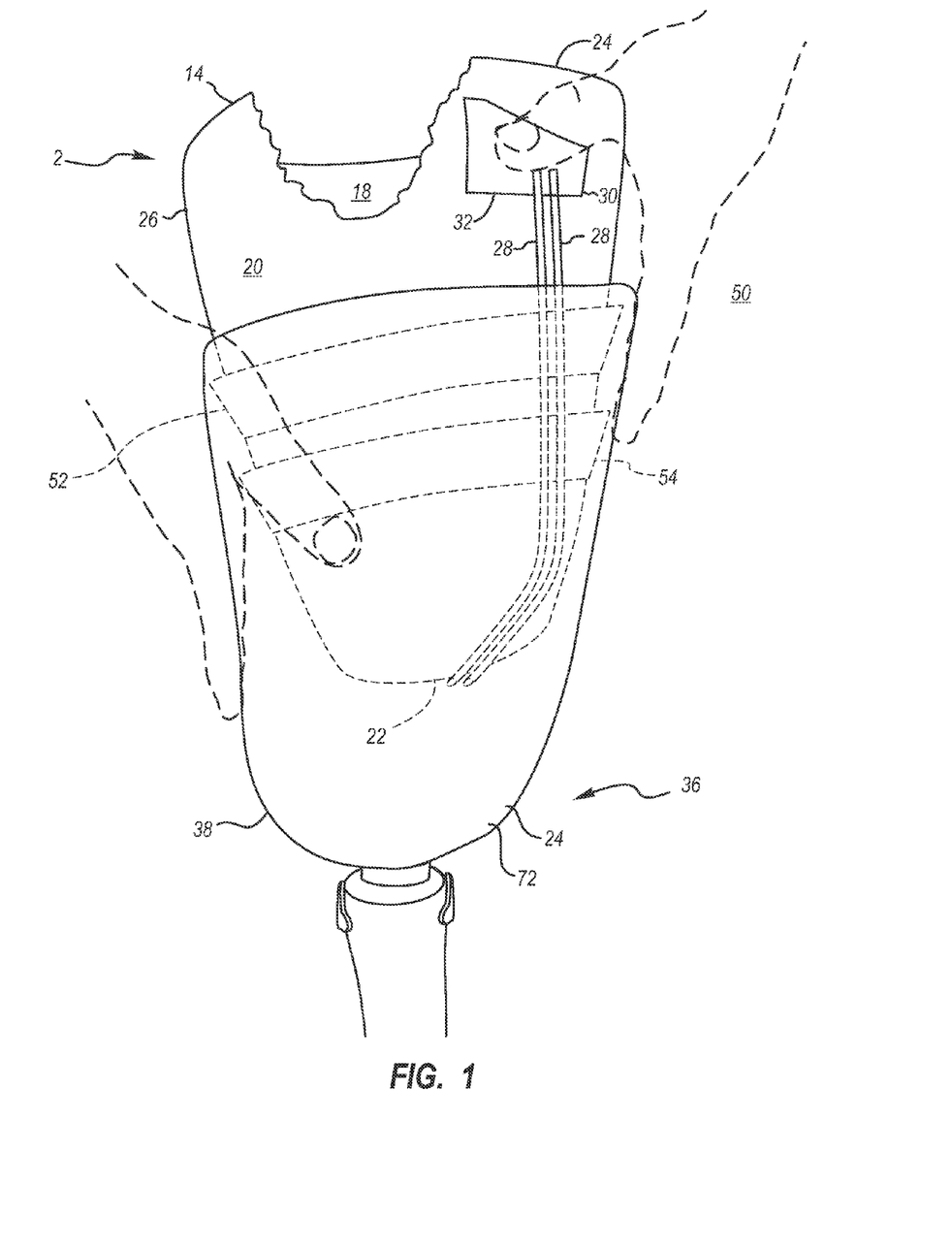
FIG. 1 is a side break-away, see-through view of an implementation of a prosthetic socket liner and a prosthesis.

Referring now to FIG. 1, in implementations a prosthetic socket liner 2 comprises a liner 14, a first socket engager 52 coupled to the liner 14 and configured to engage the surface 40 of a socket 38, a second socket engager 54 coupled to the liner 14 and configured to engage the surface 40 (shown in FIG. 3) of a socket 38, one or more air channels 28, and one or more valves 30. The liner 14 has an inner surface 18 and an outer surface 20 and the inner surface 18 is configured to engage with the skin of a residual limb of a user and the outer surface 20 is configured to engage the surface 40 of socket 38 of prosthesis 36. The air channels 28 are coupled to the liner 14 and are coupled to the one or more valves 30. In implementations the one or more valves 30 include a selective two-way valve 30. The valve in FIG. 1 is a selective two-way valve 30 and includes a flap 32. The air channels 28 extend downwardly towards a closed end 22 of the liner 14 and the air channels 28 are configured to transfer air between the outer surface 20 of the liner 14 and ambient air 50 through the one or more valves 30.

For example, in implementations the air channels 28 are configured to transfer air from an inside 74 of a cavity 72 to ambient air 50, or to a location outside the cavity 72, and vice versa, as controlled by the user through the selective two-way valve 30. Thus, in implementations the one or more air channels 28 transfer air from the closed end 22 of the liner 14 to proximate an open end 24 of the liner 14. In the implementation of FIG. 1 the socket 38 of the prosthesis 36 is a rigid socket 38 though in various implementations the prosthetic socket liner 2 may be used with flexible sockets 38. The first socket engager 52 and second socket engager 54 in implementations illustrated in FIG. 1 are flexible, circular fins which wrap around the liner 14 and are pliable enough to be bent under the pressure exerted by the socket 38 during donning and removal of the socket 38 from the residual limb. In the implementation of FIG. 1 there are two air channels 28 which are formed of tubes. In other implementations there could be a single air channel 28, or two, three, four, or more.

Likewise, in this implementation there is a first socket engager 52 and second socket engager 54 but in other implementations there may be only a first socket engager 52 or there may be more than two socket engagers such as three, four, and so forth, or even no socket engagers in some implementations. In implementations a valve 30 coupled to the air channel 28 may be included which in implementations is configured to selectively allow and disallow air to be channeled between inside the cavity 72 and outside the cavity 72.

In the implementation shown in FIG. 1 the one or more air channels 28 are coupled to the outer surface 20 of the liner 14. In other implementations the one or more air channels 28 could be coupled to the inner surface 18 of the liner 14. In other implementations, as in FIG. 6B, the one or more air channels 28 may be included within a sidewall 26 included between the inner surface 18 and outer surface 20 of the liner 16 by being molded into the sidewall 26 of the liner 16 or being integrally formed within the sidewall 26.

Figures 6A, 6B:
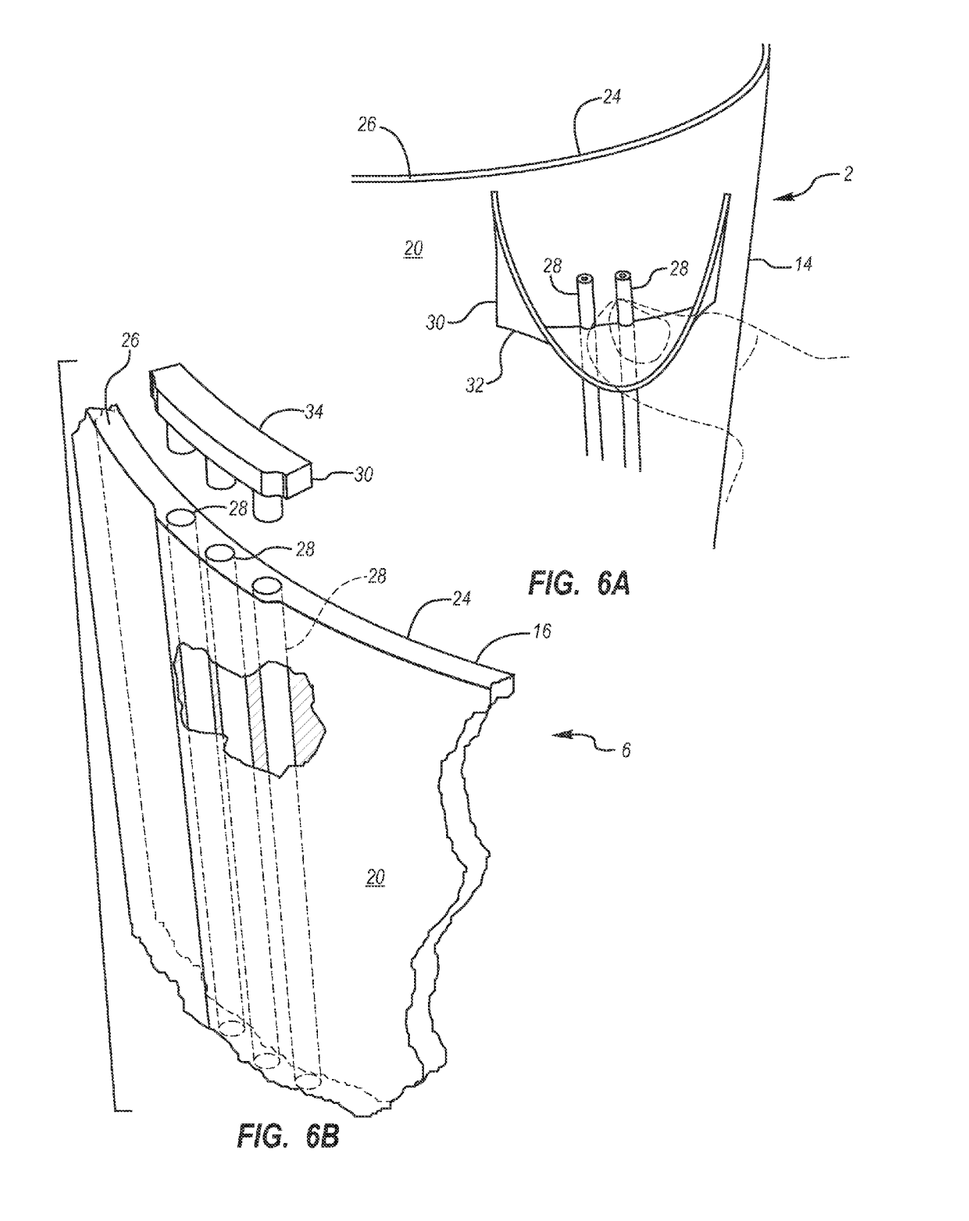
FIG. 6A is a perspective view of an implementation of a prosthetic socket liner.
FIG. 6B is an exploded perspective see-through view of an implementation of a prosthetic socket liner and an implementation of a valve.

The selective two-way valve in the implementation illustrated in FIG. 1 comprises a flap 32, which, as illustrated in FIG. 1 may be configured so that the user's thumb can be placed underneath the flap 32. In various implementations the user can place a finger underneath the flap 32 in order to open it to allow ambient air 50 to enter (via the fluid connection formed to the ambient air 50) through the air channels 28 to assist in the donning or removal of the socket 38 of the prosthesis 36. In other implementations, another structure, such as, by non-limiting example, a wedge, pin, bar, or other spreading structure, may be placed under the flap 32, or in other words between the flap 32 and an outer surface 20 of the liner 14, to enable air movement through the air channels 28. In implementations, the one or more air channels 28 may be configured to transfer air between the inner surface 18 of the liner 14 and ambient air 50 through the one or more valves 30. For instance, in implementations air may freely travel from a volume between the residual limb and the inner surface 18 of the liner 14 to ambient air 50 outside the socket 38 and liner 14 via the selective two-way valve 30. In implementations air may freely travel from a volume between the socket 38 and the outer surface 20 of the liner 14 to ambient air 50 outside the socket 38 and liner 14 via the selective two-way valve 30. In both situations, air movement may occur through the force exerted by the weight placed on the respective volume of air as a user dons the liner 14 and/or the socket 38 which increases the pressure of the respective volume of air and forces some of that air to move through the air channels 28 through the selective two-way valve 30. In particular implementations the selective two-way valve 30 is configured such that a vacuum, or low pressure area, or a suction force is created as air is expulsed from the volume of air between the inner surface 18 of the liner 14 and residual limb and/or from the volume of air between the outer surface 20 of the liner 14 and socket 38, preventing the flap 32 of the selective two-way valve 30 from opening and thus disallowing the air channels 28 from being in fluid communication with the ambient air 50. This effectively disallows ambient air 50 from traveling through the air channels 28 back into the volume between the liner 14 and socket 38 and/or liner 14 and residual limb, until a user manually lifts the flap 32, as seen in FIG. 1 and as shown in FIG. 6A. This vacuum, low pressure and/or suction force may assist in securing the liner 14 and/or socket 38 to the residual limb while it is being worn.

In some implementations a customized wedge device may be inserted in between the flap 32 and the liner 14, such that the wedge will remain seated therein of its own accord, allowing ambient air 50 to flow through the air channels 28, so that the user may use both hands to remove or don the socket 38 and/or liner 14. Various types of valves could be utilized such as, by non-limiting example, a two-way valve, a selective two-way valve 30, a flapper valve, a duckbill valve, an umbrella valve, a manual valve, a pressure sensitive valve, a computer controlled valve, an electromagnetically operated valve, and any other valve structure capable of selective activation.

Figure 2:
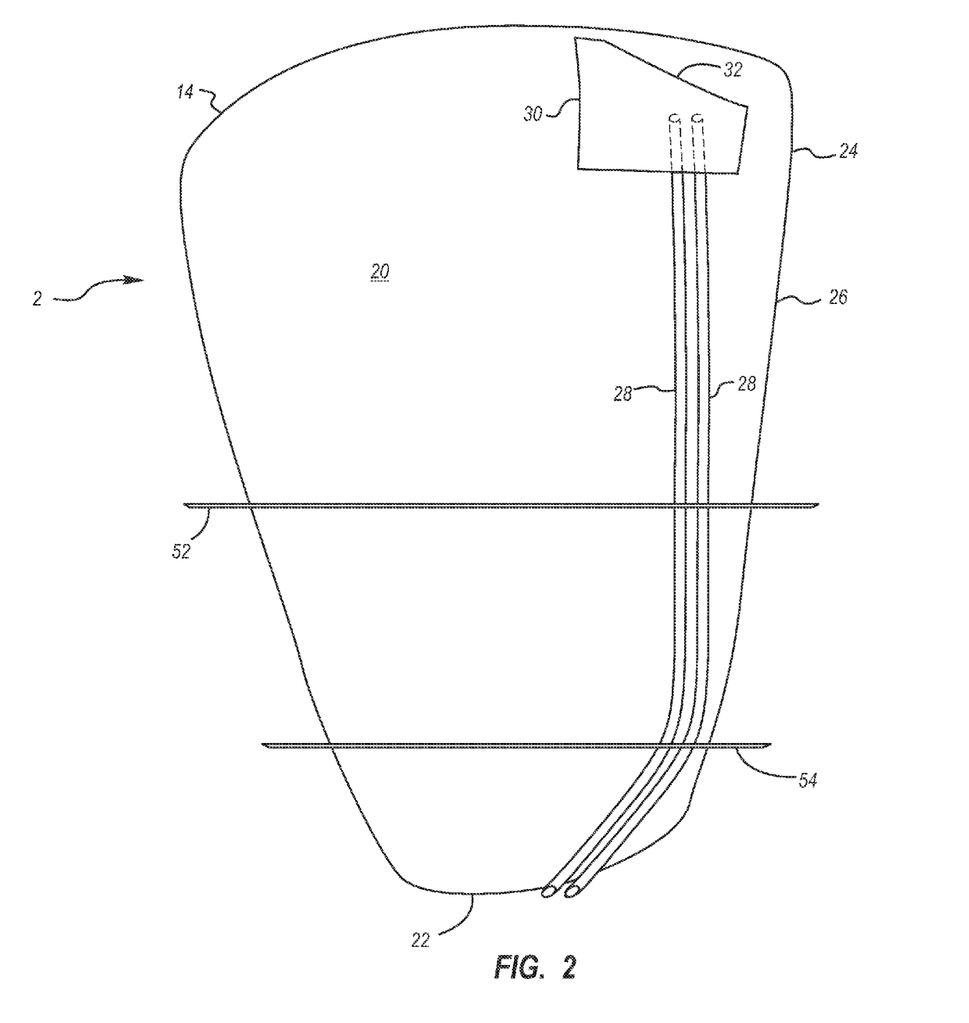
FIG. 2 is a side view of an implementation of a prosthetic socket liner.
Figure 3:
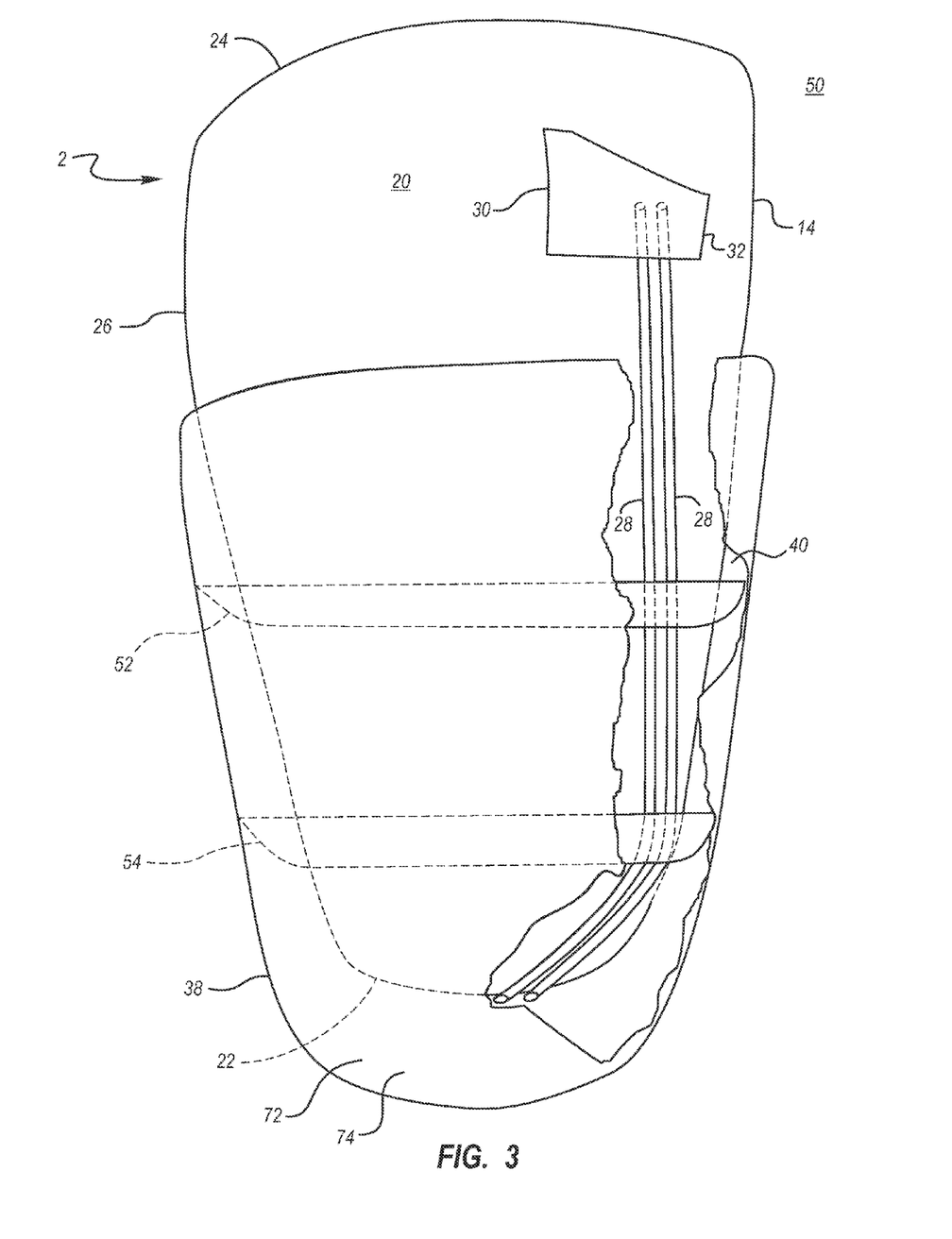
FIG. 3 is a side break-away, see-through view of an implementation of a prosthetic socket liner and a socket of a prosthesis.
Figure 4:
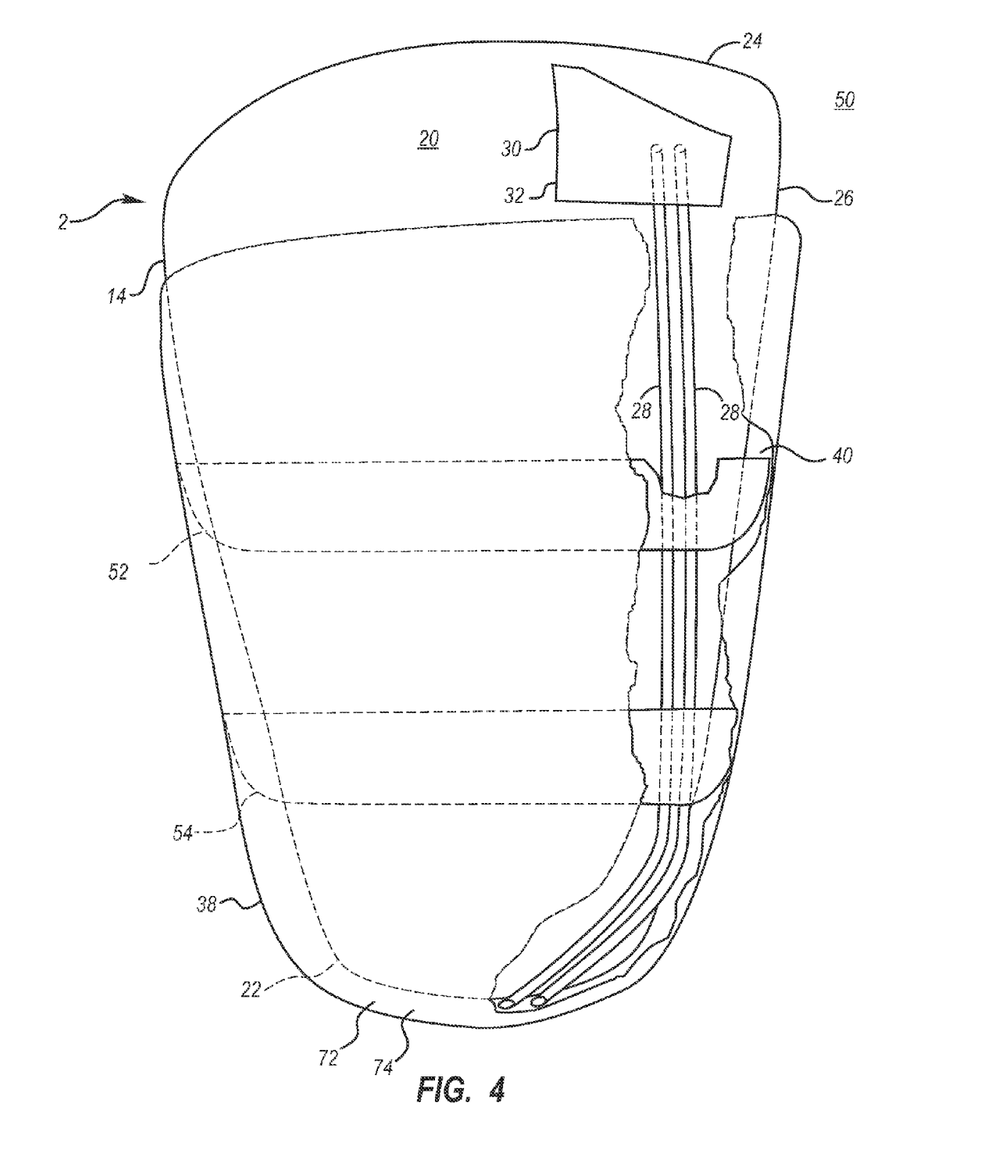
FIG. 4 is a side break-away, see-through view of an implementation of a prosthetic socket liner and a socket of a prosthesis.

FIG. 2 shows an implementation of a liner 14. FIG. 3 shows an implementation of a liner 14 partially inserted into a socket 38. FIG. 4 shows an implementation of a liner 14 more fully inserted into a socket 38. As can be seen, the first socket engager 52 and second socket engager 54 in FIG. 4 are more fully bent upwards and an open end of the socket 38 is proximate the selective two-way valve 30, and a smaller volume of air remains in an inside portion 74 of a cavity 72 in FIG. 4 than in FIG. 3. The cavity 72 is formed between the outer surface 20 of the liner 14 and a surface 40 of the socket 38 when the socket 38 and liner 14 are brought within proximity of one another.

Referring now to FIG. 4, in implementations there are two air channels 28 that travel from the selective two-way valve 30 all the way along the length of the liner 14 to a closed end 22 of the liner 14. The air channels 28 in implementations are in fluid communication, when the selective two-way valve 30 is opened, with ambient air 50 and with a volume of air between the outer surface 20 of liner 14 and the socket 38 and/or with a volume of air between the inner surface 18 of the liner 14 and a residual limb. In other words, when the selective two-way valve 30 is open (in various implementations, when the flap 32 is open), ambient air 50 can travel through the selective two-way valve 30 to the volume of air between the liner 14 and the limb and/or to the volume of air between the liner 14 and the socket 38, and air can travel from one or both of those volumes to the outside ambient air 50, as well. Thus, although the first socket engager 52 and second socket engager 54 in FIGS. 3-4 may form a substantially air-tight seal with the surface 40 of the socket 38, there can still be fluid communication between these volumes and the outside ambient air 50 via the air channels 28 and the selective two-way valve(s) 30.

In various implementations the liner 14 may have an additional valve proximate the closed end 22 of the liner so that air can freely travel from inside to outside the liner 14, or vice versa, or both. Thus, in implementations this could be a one-way or other check valve. In implementations there may simply be a hole through the thickness of the liner 14 proximate the closed end 22. Various other mechanisms could be used to facilitate fluid communication between the inside surface 18 of the liner 14 and volume between the outside surface 20 of the liner 14 and inside of the socket 38, whether one-way or two-way, selective or unselective.

FIG. 6A shows the user lifting a flap 32 of the selective two-way valve 30 in order to let ambient air 50 into the air channels 28 so that the socket 38 may be removed. Here the ends of the two air channels 28 are visible, and separating the flap 32 from the outer surface 20 of the liner 14 allows ambient air 50 to enter into the air channels 28 and flow into the space between the liner 14 and the socket 38. Although in implementations the flap 32 disallows ambient air 50 from entering the air channels 28 unless a user lifts the flap 32, in other implementations a valve 30 could freely allow air to travel in both directions through the air channels 28 without any user intervention or control.

FIG. 4 shows the socket 38 more fully donned than in FIG. 3. In implementation the selective two-way valve 30 may be covered or nearly covered by the socket 38. In such an implementation the user may need to pull the liner 14 up or push the socket 38 down a minimal amount in order to reach the selective two-way valve 30 to lift the flap 32. In other implementations the liner 14 may be custom tailored (via being a certain length or having a cut out or other opening therein or therethrough) so that it is always accessible even when the socket 38 is fully donned. The prosthetic socket liner 2 may allow a socket 38 to be donned even when the socket 38 does not have a conventional air release valve therethrough at a closed end of the socket 38 or any opening therethrough As shown in FIGS. 2-4, in implementations the first socket engager 52 and second socket engager 54 may rest at a roughly 90 degree angle with liner 14 prior to donning the socket. This may cause the first socket engager 52 and second socket engager 54 to have greater recoil/rebound properties. In other implementations the first socket engager 52 and second socket engager 54 may be coupled to the liner 14 at other angles, greater or less than 90 degrees, to acquire the proper recoil/rebound properties as desired.

In implementations the prosthetic socket liner 2 may incorporate a magnetic mechanism to primarily or secondarily affect/create suspension characteristics. In implementations, for example, the first socket engager (engager) 52 and/or second socket engager (engager) 54 may be permanently magnetically attracted to the socket 38. In other implementations, the first socket engager 52 and/or second socket engager 54 may be selectively magnetically attracted to the socket 38 such as by controlling the magnetic properties of the first socket engager 52 and/or second socket engager 54 with one or more electromagnets in the socket 38 or in the engagers 52, 54. In some implementations the engagers 52, 54 may be similarly permanently or selectively magnetically repulsed by the liner 14. In other implementations the engagers 52, 54 may be permanently or selectively magnetically attracted to the liner 14 and/or repulsed by the socket 38.

In implementations the engagers 52, 54 are at least partially metallic or contain metallic particles therein and an electromagnet (or an electromagnet in or coupled to the socket 38) selectively magnetizes the socket 38 to attract the engagers 52, 54 as desired. In various implementations, the electromagnet may be activated when the weight bearing on the socket 38 is reduced, such as when the user is sitting or lying down, in order to better secure the prosthesis 36 to the user during that time. Then, when the user stands up or is walking, the electromagnet deactivates. This may allow the user's residual limb to fit deeper into the socket 38 as needed when the user is standing or walking while providing extra sealing power and suspension when the user is sitting or lying down. The system may be configured to automatically turn the electromagnet on when the weight bearing of the socket 38 is decreased and automatically off when it is increased. This selective magnetic mechanism could be embodied at any location on or coupled to the liner 14 and/or socket 38.

In implementations engagers 52, 54 with larger diameters may provide greater and prolonged rebound against the socket 38 and/or a more substantially air-tight seal between the liner 14 and the socket 38. The orientation or angle (discussed above) of the engagers 52, 54 may affect these properties as well, as may the thickness of the engagers 52, 54, variation of the thickness of the engagers 52, 54, and any inherent curvature and/or shape of the engagers 52, 54. The ability to use a valveless socket 38, or a socket 38 with a non-functioning valve therethrough, may allow for the use of larger diameter engagers 52, 54.

Figure 5:
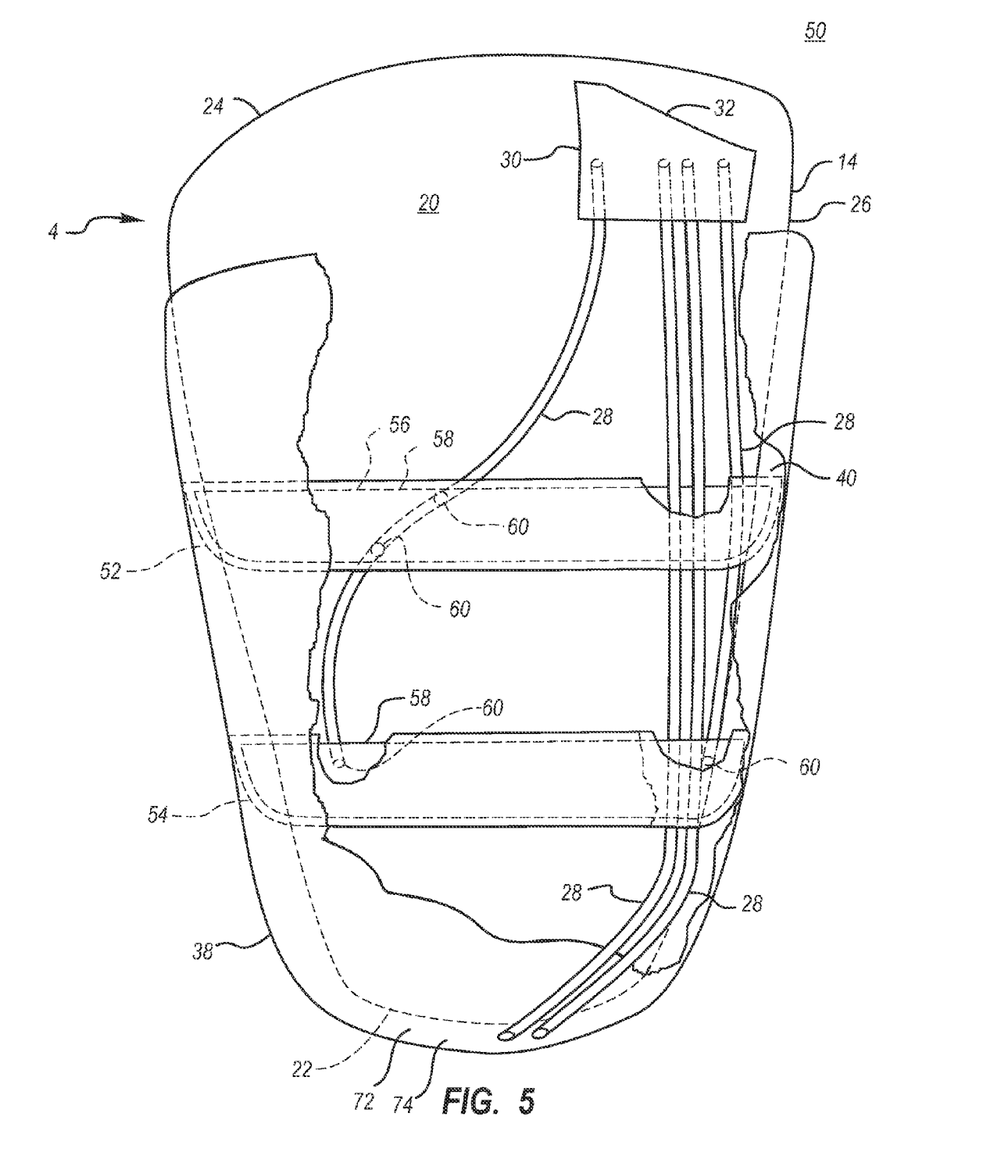
FIG. 5 is a side break-away, see-through view of an implementation of a prosthetic socket liner and a socket of a prosthesis.

Referring to FIG. 5, in various implementations, a prosthetic socket liner 4 may utilize one or more suspension members 56 which may include air bladders 58 adjacent to or in the engagers 52, 54 to receive some of the air from between the liner 14 and residual limb (and/or liner 14 and socket 38), and/or to adjust a fit of the liner 14 with the socket 38 and/or to adjust suspension properties. The suspension member 56 in implementations is coupled to the liner 14 between a first socket engager 52 and the liner 14 and includes an air bladder 58 and/or a compressible foam material. In the implementation shown, air is diverted from one more of the air channels 28 through the selective two-way valve 30 back through another air channel 28 into one or more air bladders 58 behind the engagers 52, 54. The air channel 28 which connects to the air bladders 58 incorporates one-way valves 60 at entry and exit points where it couples to the air bladder 58 closest to the open end 24 and at an entry point where it couples to the air bladder 58 closest to the closed end 22. Thus this air channel 28 may only increase the volume of air in the air bladders 58. Another air channel 28 is provided which couples the air bladder 58 nearer the closed end 22 to the selective two-way valve 30. This air channel 28 also incorporates a one-way valve 60 where it couples to the air bladder 58. The selective two-way valve 30 may be opened to selectively release some or all of the air in the air bladders 58 to adjust the suspension properties or to prepare for removal of the socket 38 and/or liner 14. The use of air bladders 58 may serve to provide or improve a substantially air-tight seal at an interface between the socket 38 and the engagers 52, 54 and thus prevent ambient air 50 from leaking into cavity 72. These implementations may also allow a user to develop a desired and adjustable degree of suspension between the residual limb and the socket 38.

Other implementations of liners 14 may utilize other methods of selectively harnessing a volume of air at one or more locations of the liner 14. These volume control mechanisms may be useful in comfortably securing the liner 14 and/or socket 38 to the residual limb as the size and/or shape of the residual limb may fluctuate over time during the day or during the user's activities. Additionally or alternatively, the suspension member 56 could include rebounding foam. The foam and/or the air bladders 58 may function to form and/or improve a substantially air-tight seal between the liner 14 and socket 38 at an interface of the socket 38 with the engagers 52, 54. In implementations the functioning of the air bladders 58 may provide for the transfer of more air from the cavity 72 and/or from a volume between the liner 14 and residual limb to ambient air 50. In implementations air from the air bladders 58 may be selectively transferred to other compartments for improving the comfort and/or fit of the prosthesis 36.

FIG. 6A is an illustration of a user opening the selective two-way valve 30 connected to the air channels 28 which shows the ends of the air channels 28. In implementations the selective two-way valve 30 may be configured such that merely increasing the pressure of the volumes of air in the cavity 72 and/or between the liner 14 and residual limb may cause air to be expelled from those volumes through the selective two-way valve 30, but air may not be channeled back to those areas/volumes via the selective two-way valve 30 until the user opens the selective two-way valve 30. For instance in the implementation of FIG. 6A the user opens the selective two-way valve 30 by lifting the flap 32 as shown to release the vacuum that normally holds the flap 32 shut. Thus air may be expelled from the cavity 72 and or from between the line 14 and residual limb automatically as the liner 14 is donned, as the socket 38 is donned, as the user stands up and puts more pressure on those volumes, as the user walks and increases pressure on those volumes, and so forth, but ambient air 50 will not travel to the cavity 72 or to the volume between the liner 14 and residual limb until the user lifts the flap 32 of the selective two-way valve 30.

FIG. 6B illustrates an implementation of a prosthetic socket liner 6 in which the air channels 28 are integrated into the sidewall 26 of the liner 16 and a selective two-way valve 30, which in this implementation is a removable plug 34, caps the tops of the air channels 28 at the open end 24 of the liner 16. In this implementation three air channels 28 are used though, as described above, in implementations only one air channel 28 may be used, or two, or four or five, or more. The illustrated implementation does not use a flap 32 to maintain the vacuum but instead a cap formed by removable plug 34 allows the user to remove the removable plug 34 when it is desired to release the vacuum and reintroduce ambient air 50 into the air channels 28 and thus into the cavity 72 and/or the volume between the liner 14 and residual limb for removal of the socket 38 and/or liner 16 or for comfort adjustment, fit adjustment, suspension adjustment or other reasons. In implementations where the air channels 28 are integrated into the sidewall 26 of the liner 16 the liner 16 may be fabricated such that the air channels 28 are molded into the sidewall 26 to begin with and thus the liner 16 may be cut to the proper length for each user/application without affecting the operation of the prosthetic socket liner 6.

Figure 7A:
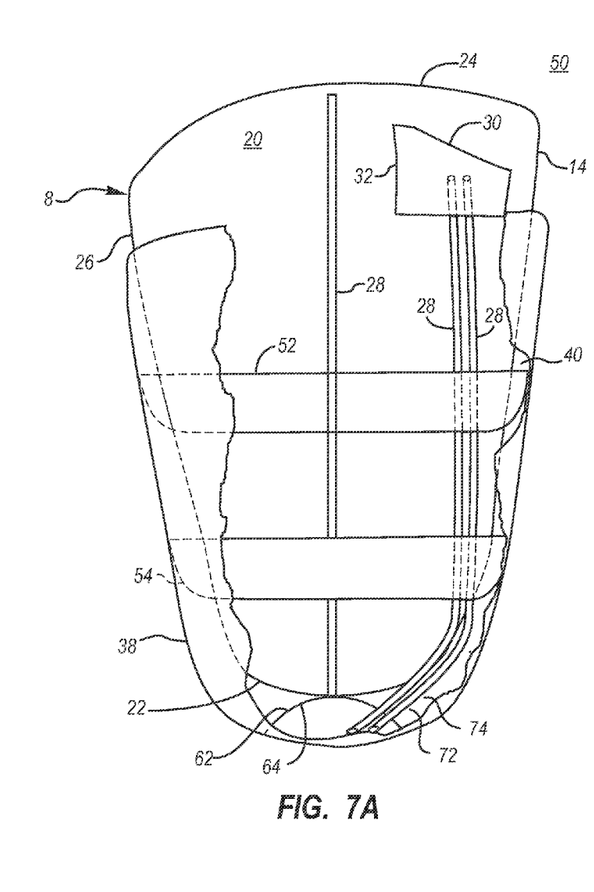
FIG. 7A is a side break-away, see-through view of an implementation of a prosthetic socket liner and a socket of a prosthesis.
Figure 7B:
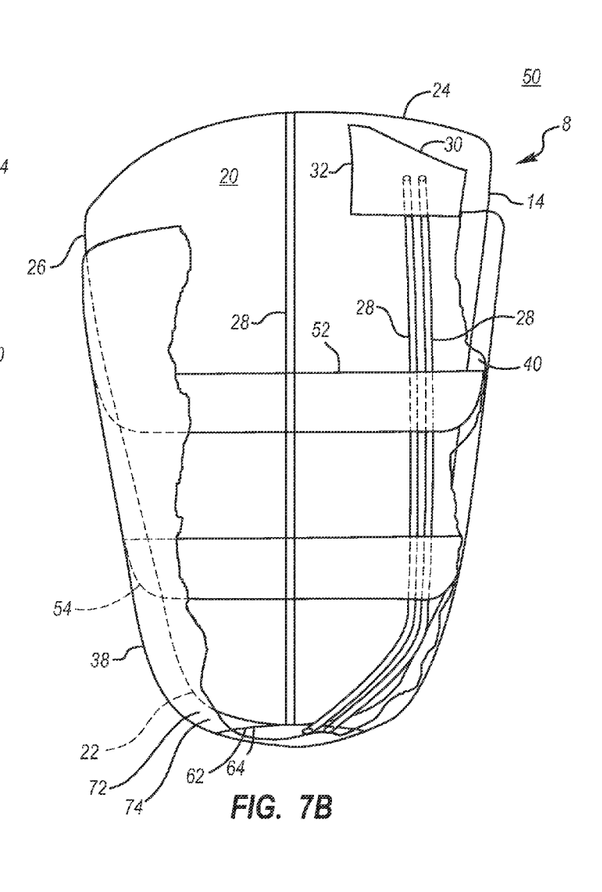
FIG. 7B is a side break-away, see-through view of an implementation of a prosthetic socket liner and a socket of a prosthesis.

In implementations a prosthetic socket liner 2, 4, 6, 8, 10, 12 includes a retainer 62 coupled to the closed end 22 of the liner 14 and configured to bias the closed end 22 of the liner 14 towards the surface 40 of the socket 38. FIG. 7A illustrates an implementation of a prosthetic socket liner 8 wherein there is a retainer 62 located at the closed end 22. The retainer selectively biases the closed end 22 towards the socket 38. The retainer 62 in this implementation is a suction cup 64. A vacuum forms when the suction cup 64 is depressed by the liner 14 being pushed downwards towards the socket 38, as shown in FIG. 7B. The vacuum tends to secure the closed end 22 to the socket 38. A dedicated two-way valve to the suction cup 64 may be utilized to provide fluid communication from ambient air 50 to inside the vacuum between the suction cup 64 and the socket 38 to enable the user to lessen, increase, or release the vacuum, at the user's discretion. For instance in the implementation of FIG. 7A, a dedicated two way valve may be coupled to the vacuum via an air channel 28 that travels down the liner 14 to provide this fluid communication between ambient air 50 and inside the vacuum when the user desires such communication. When the suction cup 64 is depressed, air exits the system into ambient air 50 via the dedicated two way valve. Ambient air 50 does not reenter the vacuum without the user opening the dedicated two way valve, thus maintaining the vacuum. To release, increase, or lessen the vacuum, the user operates the dedicated two way valve to allow ambient air 50 outside the system to travel to the vacuum (or from the vacuum). The vacuum when released causes the suction cup 64 to rebound to its original non-depressed configuration as illustrated in FIG. 7A. In other implementations the vacuum may operate similarly but may do so via fluid communication with the main selective two-way valve 30 instead of through a dedicated two way valve. In such implementations the depression of the suction cup 64 expels air and creates the vacuum—the air being expelled through the main selective two-way valve 30 to outside the system, and opening the main selective two-way valve 30 operates to release or lessen the vacuum by communicating ambient air 50 from outside the system to the vacuum.

Figure 8:
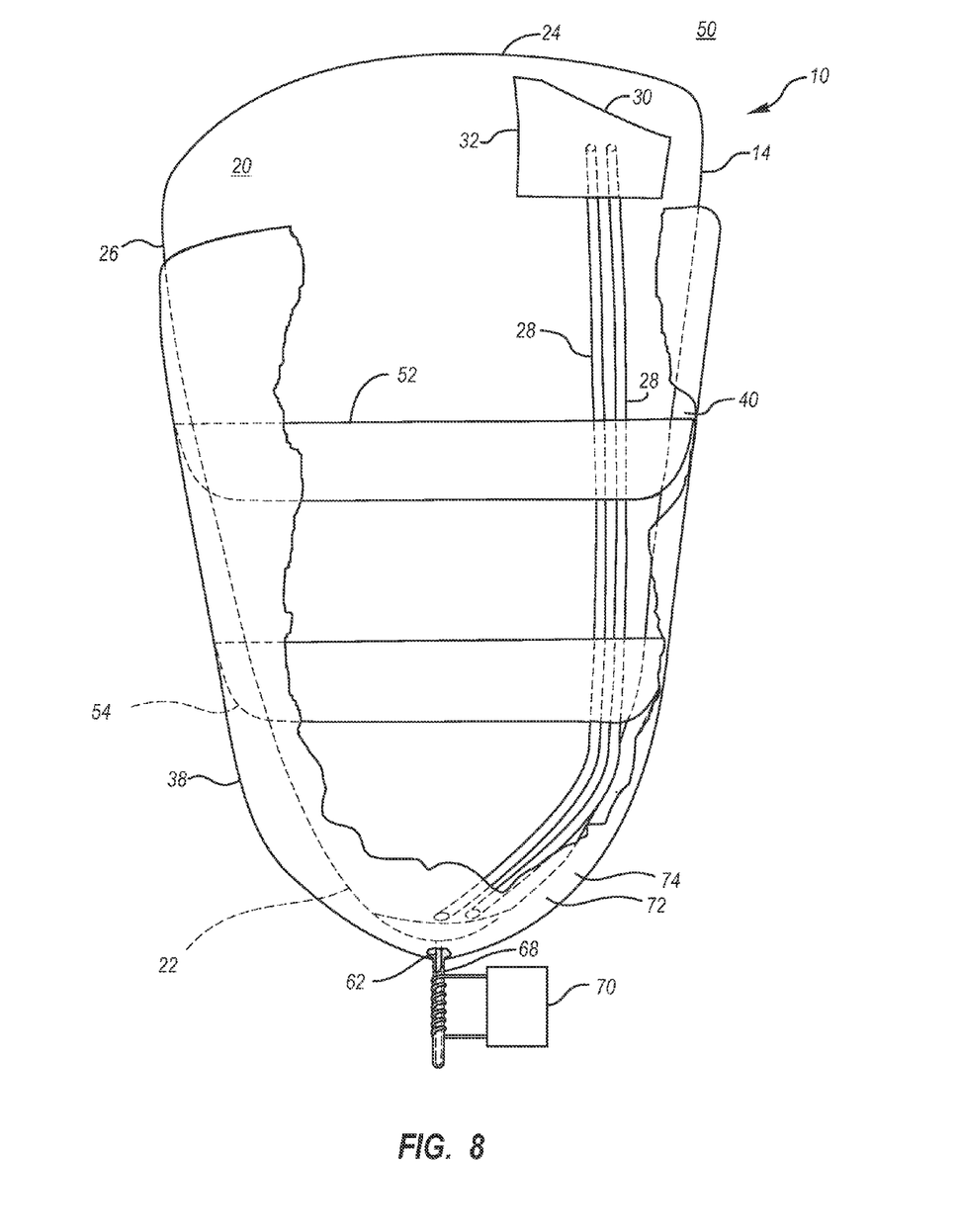
FIG. 8 is a side break-away, see-through view of an implementation of a prosthetic socket liner and a socket of a prosthesis.

FIG. 8 illustrates an implementation of a prosthetic socket liner 10 utilizing a metal pin 68 and an umbrella receiver to secure the closed end 22 to the socket 38. An electromagnet 70 surrounding the metal pin 68, when activated, secures the metal pin 68 in a cavity in the socket 38 sized to receive the metal pin 68—thereby securing the liner 14 to the socket 38 via the metal pin 68. When the electromagnet 70 is deactivated, the metal pin 68 is free to move in or out of the cavity and the metal pin 68 no longer secures the liner 14 to the socket 38. In implementations the electromagnet 70 is activated during non-weight bearing periods and deactivated during weight bearing periods, thus ensuring the socket 38 remains attached to the residual limb when, for instance, the user is sitting or lying down and not putting weight on the prosthesis 36. In the implementation shown in FIG. 8 there are no holes or openings through the socket 38 apart from the opening that receives the residual limb and liner 14. In implementations the umbrella receiver and metal pin 68 design disclosed herein could be used alone or in combination with the magnetic or metallic engagers 52, 54 described above.

Figure 9A:
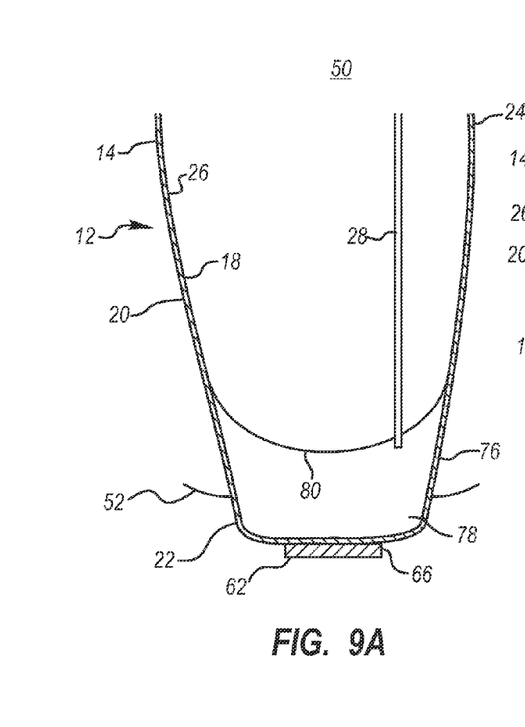
FIG. 9A is a side see-through view of an implementation of a prosthetic socket liner.
Figure 9B:
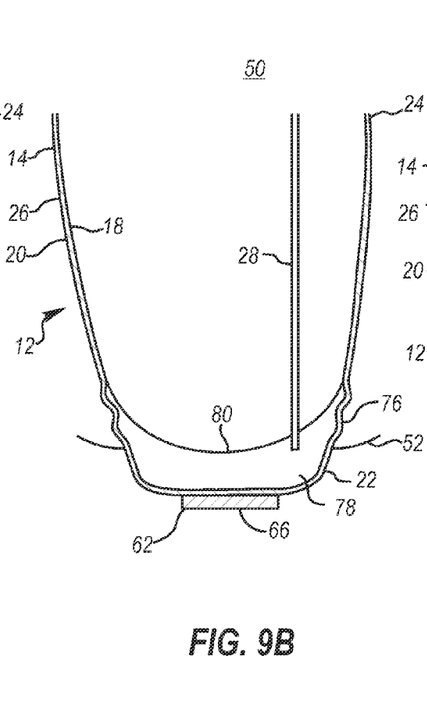
FIG. 9B is a side see-through view of an implementation of a prosthetic socket liner in a partially compressed configuration.
Figure 9C:
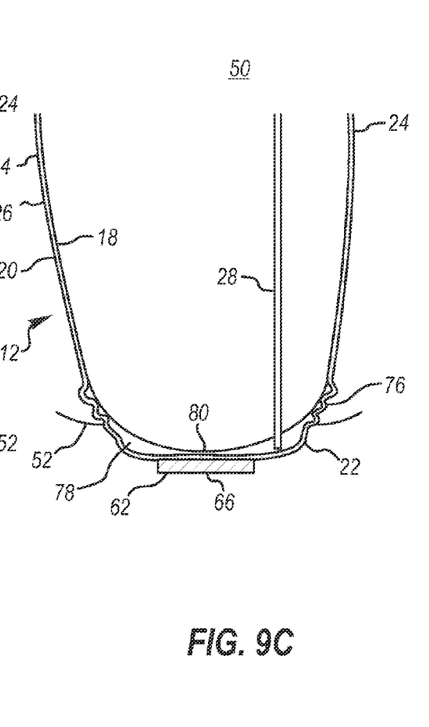
FIG. 9C is a side see-through view of an implementation of a prosthetic socket liner in a fully compressed configuration.

FIGS. 9A-9C illustrate an implementation of a prosthetic socket liner 12 which includes a compressible section 76. A cavity 78 is formed by the sidewall 26 and a cavity wall 80 at the closed end 22 of the liner 14. An air channel 28 communicates air from within the cavity 78 to ambient air 50 and vice versa, as desired by the user, and may be used in conjunction with any variety of valves such as a selective two-way valve 30, a flap 32, a removable plug 34, and any other disclosed in this document. When pressure is placed downwards on the cavity (i.e., in the direction from the open end 24 towards the closed end 22), such as when a user has already donned the liner 14 but is now donning the socket 38, the compressible section 76 may compress and force air from within the cavity 78 to exit to ambient air 50 via the air channel 58 and valve. In implementations this may help in the adjustment of a proper fit for a user. For example, in implementations the cavity wall 80 indicates the depth to which a user's residual limb reaches inside the liner 14 towards the closed end 22. In implementations the girth of a user's residual limb, in relation to the length of the residual limb, may prevent the user's residual limb from reaching the bottom of the inside of a socket 38 before the girth of the user's residual limb stops downward movement. In such instances, the prosthetic liner 12 may allow the liner 14 to reach the bottom of the inside of the socket 38 and then the compressible section 76 may compress, using the above described mechanisms or other similar mechanisms, until the residual limb's girth prevents further downward movement or until a proper comfort and use level is achieved. In implementations the cavity 78 may be partially or entirely filled with a compressible foam section.

In the implementation shown in FIGS. 9A-9C a retainer 62 may be provided in the form of a magnet 66 which may be utilized to bias the closed end 22 towards the socket 38. Any other retainer implementation disclosed herein may be utilized as well. In implementations the prosthetic socket liners 2, 4, 6, 8, 10, 12 could use multiple selective two-way valves 30 instead of just one. In other implementations the prosthetic socket liners 2, 4, 6, 8, 10, 12 may be donned by simply sliding them over the residual limb, as a sock, without needing to be inverted and donned via inversion over the residual limb, since in implementations air between the liner 14, 16 and residual limb may exit automatically via one or more air channels 28 and valves. In implementations all of the air channels 28, or multiple air channels 28, may be routed to a single air channel 28 which is in fluid communication with a valve, such as a selective two-way valve.

In implementations a smooth first liner is placed over a residual limb, a sock is placed over the first liner which fits over the first liner but extends a shorter distance up the residual limb than the first liner, and a smooth second liner is placed over the sock and is longer than the sock such that its upper portion rests flush against the first liner. Because the second liner is longer than the sock and rests flush against the first liner above the sock, a seal is formed at the juncture of the first and second liner that acts as a continuous flapper valve located all the way around the residual limb at the top edges of the first and second liner. The second liner may have air channels 28 that extend from a closed end 22 into the sock portion located between the first and second liners. In such implementations, the sock may act as an air channel 28 by allowing air to travel up the residual limb via the sock and exit via the continuous flapper valve. Thus when a socket 38 is donned, air may be channeled from the cavity 72 through the sock and outside the system to ambient air 50. Ambient air 50 cannot reenter the sock to travel back down to the cavity 72 unless the user opens the flapper valve such as by separating the second liner from the first liner with a finger.

In implementations one or more air channels 28, or an additional air channel 28, may be used to expulse and impulse air into and out of the system with a commercial or other mechanical pump to achieve elevated vacuum fit and suspension. The prosthetic socket liner 2, 4, 6, 8, 10, 12 may be configured with one or more connection devices for a commercial or other mechanical vacuum source to connect to it to pump air in and/or out through the air channels 28.

All of the valving, switching and monitoring of both positive and negative pressures as well as temperature and step cycles could be controlled and archived by a computer system or microcontroller for any of the implementations disclosed herein. Printouts of relevant data could also be recorded and provided for analysis via various memory devices incorporated in the socket and/or liner or other components in electrical communication therewith.

The prosthetic socket liner 2, 4, 6, 8, 10, 12 in implementations disclosed herein may be made of conventional materials used to make goods similar to these in the art, such as, by non-limiting example, polymers, composites, metals, ceramics, and the like. In implementations the liner 14, 16 comprises a layer of silicone at its inner surface 18 (i.e., the surface that engages skin of the residual limb), and a TEFLON polymer outer surface 20, and the selective two-way valve 30 or flap 32 is comprised of silicone. In other implementations, a line of silicone is placed between air channels 28 along their longest length to provide rigidity and support so that the air channels 28 do not collapse and close off during use. In some implementations the air channels 28 may be attached to the liner 14 with a glue and the flap 32 of the selective two-way valve 30 may also be attached to the liner 14 with a glue. Those of ordinary skill in the art will readily be able to select appropriate materials and manufacture these products from the disclosures provided herein.

In implementations the liner 14, 16 is formed of a substantially non-air-permeable material.

Implementations of a method of donning a socket 38 of a prosthesis 36 may include donning a liner 14, 16 of a prosthetic socket liner 2, 4, 6, 8, 10, 12 over a portion of a residual limb of a user, opening a valve on the liner 14, 16, inserting the liner 14, 16 into a socket 38 of a prosthesis 36 with the valve open, and closing the valve. In implementations the method may include forming one of a lubricated surface and an airtight seal between an outer surface 20 of the liner 14, 16 and a surface 40 of the socket 38.

Elements, features, and limitations of any of the implementations disclosed herein may be combined with those of other implementations.

In places where the description above refers to particular implementations of prosthetic socket liners, it should be readily apparent that a number of modifications may be made without departing from the spirit thereof and that these implementations may be applied to other prosthetic socket liners.

What is claimed is:

1. A prosthetic socket liner, comprising:

a liner comprising an inner surface and an outer surface and one or more valves, the inner surface configured to engage with skin of a residual limb of a user and the outer surface configured to engage a surface of a socket of a prosthesis; and one or more air channels coupled to the one or more valves and comprised within a sidewall between the inner surface and outer surface of the liner, the one or more air channels extending downwardly towards a closed end of the liner, the one or more air channels configured to transfer air located between the outer surface of the liner and the surface of the socket with ambient air through the one or more valves;

wherein the one or more valves comprise a selective two-way valve and wherein the outer surface of the liner is non-air-permeable.

2. The device of claim 1, wherein the one or more air channels are at least two air channels and are further configured to transfer air located between the inner surface of the liner and the skin of the residual limb with ambient air through the one or more valves.

3. The device of claim 1, further comprising a first socket engager coupled to the liner and configured to engage the surface of the socket.

4. The device of claim 1, wherein the one or more air channels transfer air from the closed end of the liner to proximate an open end of the liner.

5. The device of claim 1, further comprising a suspension member coupled to the liner between a first socket engager and the liner and comprising one of an air bladder and a compressible foam.

6. The device of claim 1, further comprising a retainer coupled to the closed end of the liner and configured to bias the closed end of the liner towards the surface of the socket.

7. The device of claim 1, wherein the liner is comprised of a substantially non-air-permeable material.

8. A prosthetic socket liner, comprising:

a liner configured to engage a residual limb of a user, the liner comprising a valve;

a first socket engager coupled to the liner and configured to engage a socket of a prosthesis;

an air channel comprised within a sidewall between an inner surface and an outer surface of the liner and configured to channel air between an inside of a cavity and a location outside the cavity, the cavity located between the liner and the socket; and wherein the valve is coupled to the air channel and is configured to selectively allow and disallow air to be channeled between inside the cavity and outside the cavity; and wherein the valve is a selective two-way valve and wherein the outer surface of the liner is non-air-permeable.

9. The device of claim 8, further comprising a second socket engager coupled to the liner and configured to engage the socket.

10. The device of claim 8, wherein the first socket engager comprises a flexible, circular fin extending outwardly from the liner.

11. The device of claim 8, wherein the valve is one of: a flap held closed by low pressure formed within the cavity; and a removable plug.

12. The device of claim 8, wherein the air channel channels air from a closed end of the liner to proximate an open end of the liner.

13. The device of claim 8, further comprising a suspension member coupled to the liner between the first socket engager and the liner.

14. The device of claim 8, wherein the liner is comprised of a substantially non-air-permeable material.

15. A method of donning a socket of a prosthesis, comprising:

donning a liner of a prosthetic socket liner over a portion of a residual limb of a user;

opening a valve comprised in the liner;

inserting the liner into a socket of a prosthesis with the valve open;

in response to inserting the liner into the socket, transferring air located between an outer surface of the liner and a surface of the socket to ambient air through the valve and through one or more air channels comprised within a sidewall of the liner between an inner surface and an outer surface of the liner;

closing the valve; and forming one of a lubricated surface and an air-tight seal between an outer surface of the liner and a surface of the socket, and wherein the outer surface of the liner is non-air-permeable.

* * * * *